United States Patent
Gogin et al.

(10) Patent No.: US 8,452,062 B2
(45) Date of Patent: May 28, 2013

(54) RESPIRATION DETERMINATION APPARATUS FOR DETERMINING RESPIRATION BASED ON BRONCHIAL TREE IMAGE DATA

(75) Inventors: Nicolas Pierre Bruno Gogin, Paris (FR); Niels Nijhof, Eindhoven (NL); Cecile Anne Marie Picard, Sevres (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 261 days.

(21) Appl. No.: 12/935,024

(22) PCT Filed: Mar. 30, 2009

(86) PCT No.: PCT/IB2009/051319
§ 371 (c)(1),
(2), (4) Date: Sep. 28, 2010

(87) PCT Pub. No.: WO2009/122343
PCT Pub. Date: Oct. 8, 2009

(65) Prior Publication Data
US 2011/0013816 A1 Jan. 20, 2011

(30) Foreign Application Priority Data

Apr. 3, 2008 (EP) .................................. 08305082
Sep. 16, 2008 (EP) .................................. 08305555

(51) Int. Cl.
*G06K 9/00* (2006.01)

(52) U.S. Cl.
USPC ........................................................ 382/128

(58) Field of Classification Search
None
See application file for complete search history.

(56) References Cited

U.S. PATENT DOCUMENTS

| 5,088,501 | A | 2/1992 | Niewisch |
| 2003/0228344 | A1 | 12/2003 | Fields et al. |
| 2004/0152974 | A1 | 8/2004 | Solomon |
| 2004/0252870 | A1* | 12/2004 | Reeves et al. ................ 382/128 |
| 2005/0182295 | A1 | 8/2005 | Soper et al. |
| 2007/0013710 | A1* | 1/2007 | Higgins et al. .............. 345/581 |
| 2007/0049817 | A1 | 3/2007 | Preiss et al. |
| 2007/0071301 | A1* | 3/2007 | Kiraly et al. ................ 382/131 |
| 2007/0100223 | A1 | 5/2007 | Liao et al. |
| 2007/0249931 | A1 | 10/2007 | Fain et al. |
| 2008/0212852 | A1* | 9/2008 | Sun et al. .................... 382/128 |

FOREIGN PATENT DOCUMENTS

| JP | 2002186678 A | 7/2002 |
| WO | 2006000953 A1 | 1/2006 |
| WO | 2007069168 A2 | 6/2007 |

OTHER PUBLICATIONS

Ma et al., "Comparing Image-Based Respiratory Motion Correction Methods for Anatomical Roadmap Guided Cardiac Electrophysiology Procedures", Functional Imaging and Modeling of the Heart Lecture Notes in Computer Science, vol. 6666, 2011, pp. 55-62.*
Macklin, C.: "X-Ray Studies on Bronchial Movements"; The American Journal of Anatomy, vol. 35, No. 2, 1925, pp. 303-329.

(Continued)

*Primary Examiner* — Barry Drennan
*Assistant Examiner* — Tahmina Ansari

(57) ABSTRACT

A respiration determination apparatus includes a bronchial tree image data set providing unit which provides a bronchial tree image data set showing a bronchial tree. The apparatus further includes a bronchial tree detection unit for detecting the bronchial tree in the bronchial tree image data set, and a respiratory information determination unit for determining information about the respiration from the detected bronchial tree.

12 Claims, 4 Drawing Sheets

OTHER PUBLICATIONS

Penney et al: "A Comparison of Similarity Measures for Use in 2-D-3D Medical Image Registration"; IEEE Transactions Medical Imaging, vol. 17, No. 4, Aug. 1998, pp. 586-595.

Tschirren et al: "Segmentation, Skeletonization, and Branchpoint Matching-A Fully Automated Quantitative Evaluation of Human Intrathoracic Airway Trees"; Medical Image and Computing and Computer Assisted Intervention—Miccai, LNCS vol. 2489, 2002, pp. 12-19.

Low et al: "A Method for the Reconstruction of Four-Dimensional Synchronized CT Scans Acquired During Free Breathing"; Medical Physics, vol. 30, No. 6, Jun. 2003, pp. 1254-1263.

Buliev et al: "Estimation of the Heart Rerspiratory Motion With Applications for Cone Beam Computed Tomography Imaging: A Simulation Study"; IEEE Transactions on Information Technology in Biomedicine, vol. 7, No. 4, Dec. 2003, pp. 404-411.

* cited by examiner

RESPIRATION DETERMINATION APPARATUS FOR DETERMINING RESPIRATION BASED ON BRONCHIAL TREE IMAGE DATA

FIELD OF THE INVENTION

The present invention relates to a respiration determination apparatus, a respiration determination method and a respiration determination computer program for determining respiration of a person.

BACKGROUND OF THE INVENTION

U.S. Pat. No. 5,088,501 discloses an arrangement for acquiring a signal corresponding to respiratory movement, which includes a pneumatic respiratory belt which generates a mechanical pressure signal and a pressure transducer which converts the incoming mechanical pressure signal into an optical signal using a flexible membrane. The flexible membrane is deformed by the pressure signal and has a reflective surface thereon so that a modulated light signal is generated corresponding to the pressure signal. This modulated light signal corresponds to the respiratory movement and is used together with a magnetic resonance imaging system for synchronizing or gating a generation of an image of a person, in order to avoid motion artifacts in the image caused by respiration.

This arrangement has the drawback that in addition to a device for providing an image a pneumatic respiratory belt is needed, which generates a signal comprising information about respiration.

SUMMARY OF THE INVENTION

It is an object of the present invention to provide a respiration determination apparatus, a respiration determination method and a respiration determination computer program for determining respiration of a person, wherein information about respiration can be obtained, without needing a pneumatic respiratory belt.

In a first aspect of the present invention, a respiration determination apparatus for determining respiration of a person, the apparatus comprising:
  a bronchial tree image data set providing unit for providing a bronchial tree image data set showing a bronchial tree,
  a bronchial tree detection unit for detecting the bronchial tree in the bronchial tree image data set,
  a respiratory information determination unit for determining information about the respiration from the detected bronchial tree.

Since the information about respiration is determined based on the detected bronchial tree, which has been detected in the provided bronchial tree image data set, information about respiration, which is, for example, a respiratory phase or a movement of the bronchial tree, can be obtained without needing a pneumatic respiratory belt. In particular, it is possible to obtain the information about respiration based only on the bronchial tree image data set, i.e. it is not necessary to use further devices for determining information about respiration. Therefore, for example, the thorax of a person can be imaged by the bronchial tree image data set providing unit and the same image can be used for, for example, diagnostic purposes and for determining information about respiration.

The bronchial tree is the entire bronchial tree or a part of the bronchial tree. Preferentially, the term "bronchial tree" refers to the first bifurcation being the tracheal bifurcation of the bronchial tree and/or to secondary bifurcations. It is further preferred that the bronchial tree detection unit is adapted to detect a contour of at least a part of the bronchial tree, which is preferentially a contour enclosing the tracheal bifurcation. The use of the tracheal bifurcation has the advantage that it is generally easier detectable in the bronchial tree image data set, in particular, if the bronchial tree image data set is an X-ray image data set, thereby further improving the quality of the information about respiration.

In a preferred embodiment, the bronchial tree image data set comprises several bronchial tree images showing the bronchial tree at different points in time, the bronchial tree detection unit is adapted to detect a movement of the bronchial tree in the bronchial tree image data set, and the respiratory information determination unit is adapted to determine the movement of the bronchial tree as the information about the respiration. It is further preferred that the bronchial tree detection unit is adapted to segment the bronchial tree in the several bronchial tree images showing the bronchial tree at different points in time for generating segmented bronchial trees that correspond to different points in time, which form the bronchial tree movement. The determined movement is preferentially described as a translation and/or a rotation of the bronchial tree. If the bronchial tree image data set is a set of two-dimensional projection images, which have been acquired at different points in time, the determined movement of the bronchial tree is preferentially described as a translation and/or a rotation in the projection plane of the two-dimensional projection images. Since the bronchial tree moves with respiration and, thus, the movement of the bronchial tree is caused by respiration, the movement of the bronchial tree is information about the respiration, which can be obtained with good quality from the bronchial tree image data set.

In an embodiment, the segmentation of the bronchial tree is performed by extracting contours in the bronchial tree image data set and by grouping these contours together such that the grouped contours are consistent with a priori information about the anatomy of the bronchial tree, for example, such that they are consistent with a priori information about the bronchial tree outline. In another embodiment, the segmentation of the bronchial tree can be performed by using other, known segmentation methods.

It is further preferred that the respiration information determination unit comprises a bronchial tree model providing unit for providing a bronchial tree model, which depends on a respiratory phase, and a respiratory phase determination unit for determining a respiratory phase of the person by determining the respiratory phase, at which the bronchial tree model is most similar to the detected bronchial tree, wherein the determined respiratory phase is the information about respiration. It is further preferred that the bronchial tree model is formed as a set of different bronchial tree models for different respiratory phases, wherein the respiratory phase determination unit is adapted to determine a respiratory phase of the person by determining the bronchial tree model, which is most similar to the detected bronchial tree, wherein the respiratory phase of the most similar bronchial tree model is determined as the information about respiration. The similarity is preferentially determined by using a similarity measure like the sum of squared differences or a correlation. This allows determining the respiratory phase as information about respiration with high accuracy.

It is further preferred that the bronchial tree image data set providing unit is a fluoroscopy image data set providing unit for providing a fluoroscopy image data set being the bronchial tree image data set.

The fluoroscopy image data set providing unit is preferentially an X-ray fluoroscopy device. This allows generating the bronchial tree image data set in real time, wherein preferentially the bronchial tree can be detected and the information about respiration can be determined dynamically and in real time. The bronchial tree image data set is preferentially a set of two-dimensional projection images, which are acquired successively.

It is further preferred that the respiration determination apparatus comprises a representation providing unit for providing a representation of a heart of the person and a heart image generation unit for generating an image showing the representation of the heart depending on the determined information about the respiration. It is preferred that the representation providing unit comprises a heart image data set providing unit for providing a heart image data set showing the heart, wherein the representation providing unit is adapted to provide the representation of the heart based on the heart image data set. It is further preferred that the representation providing unit comprises a segmentation unit for segmenting the heart in the heart image data set for providing the representation of the heart. Known segmentation methods, which can be used for segmenting the heart in the heart image data set, are, for example, a region growing method or the use of a general adaptive heart shape model, which is adapted to the current heart image data set. This allows providing a representation of the heart, which is preferentially a two- or three-dimensional heart model, which fits to the heart being currently imaged.

In an embodiment, a model of the heart is provided without performing a segmentation step, i.e. the segmentation step is optional. The model of the heart can simply be a function that gives the three-dimensional deformation of the model at each phase.

The term "heart" indicates the entire heart or a part of the heart only. This part can be any part of the heart. Preferentially, the term "heart" indicates the left atrium, because the left atrium is important in detecting and treating cardiac arrhythmia.

The heart image data set providing unit is preferentially a computed tomography imaging device, a magnetic-resonance imaging device, a nuclear imaging device like a positron emission tomography device or a single photon emission tomography device or another imaging device for generating an image data set of the heart. The heart image data set providing unit can also be a storing unit, in which the heart image data set is stored already. Also the representation providing unit can be a storing unit, in which the representation of the heart is stored already, but preferentially the representation of the heart shows a heart of current person, which is determined by using the heart image data set provided by the heart image data set providing unit.

It is further preferred that the heart image generation unit comprises a heart movement determination unit for determining a movement of the heart from the determined information about the respiration and a heart moving unit for moving the representation of the heart in accordance with the determined movement of the heart, wherein the heart image generation unit is adapted to generate an image showing the moving representation of the heart. This allows generating an image of the heart, which shows a representation of the heart, which moves according to respiration.

It is further preferred that
the bronchial tree image data set comprises several bronchial tree images showing the bronchial tree at different points in time,
the bronchial tree detection unit is adapted to detect a movement of the bronchial tree in the bronchial tree image data set,
the respiratory information determination unit is adapted to determine the movement of the bronchial tree as the information about the respiration,
the heart movement determination unit is adapted to determine the movement of the heart as the determined movement of the bronchial tree. If it is assumed that the heart, in particular, the left atrium, moves rigidly with the bronchial tree, in particular, the tracheal bifurcation, the movement of the heart and the movement of the bronchial tree are the same and the heart movement determination unit is adapted to determine the movement of the heart, in particular, the movement of the left atrium, as the movement of the bronchial tree, in particular, of the tracheal bifurcation. The heart moving unit is then adapted to move the heart by adding the determined movement of the bronchial tree to the representation of the heart, which is shown by the heart image generation unit.

It is further preferred that
the representation providing unit is adapted to provide different representations of the heart, which correspond to different respiratory phases,
the respiration information determination unit comprises:
a bronchial tree model providing unit for providing a bronchial tree model, which depends on a respiratory phase,
a respiratory phase determination unit for determining a respiratory phase of the person by determining the respiratory phase, at which the bronchial tree model is most similar to the detected bronchial tree, wherein the determined respiratory phase is the information about respiration,
the bronchial tree image data set comprises several bronchial tree images showing the bronchial tree at different points in time,
the bronchial tree detection unit is adapted to detect the bronchial tree in the several bronchial tree images,
the respiratory phase determination unit is adapted to determine the respiratory phase for the several bronchial tree images for determining several respiration phases that correspond to the different points in time,
the heart movement determination unit is adapted to determine a movement of the heart as a series of the representations of the heart, which correspond to the determined several respiratory phases, sorted in accordance with their respective points in time. This also allows determining a movement of the heart caused by respiration.

It is further preferred that
the bronchial tree image data set comprises several bronchial tree images showing the bronchial tree at different points in time,
the bronchial tree detection unit is adapted to detect a movement of the bronchial tree in the bronchial tree image data set, and
the respiratory information determination unit is adapted to determine the movement of the bronchial tree as the information about the respiration,
the determined movement of the bronchial tree is periodical and comprises several moving phases, wherein the heart image generation unit is adapted to image the representation of the heart, if the bronchial tree is in a predetermined moving phase. The moving phases of the movement of the bronchial tree correspond to the respiration phases, and the representation of the heart is therefore preferentially only shown, for example, overlaid over the bronchial tree image data set, which is preferentially a temporal sequence of two-dimensional fluoroscopy projection images, if a certain respiration phase is present. For example, the representation of the heart is only shown at end-expiration.

It is further preferred that the respiration information determination unit comprises:

a bronchial tree model providing unit for providing a bronchial tree model, which depends on a respiratory phase, a respiratory phase determination unit for determining a respiratory phase of the person by determining the respiratory phase, at which the bronchial tree model is most similar to the detected bronchial tree, wherein the determined respiratory phase is the information about respiration, the heart image generation unit is adapted to image the representation of the heart, if the determined respiratory phase is similar to a predetermined respiratory phase. Also this allows showing the heart only, if the certain respiratory phase has been determined, for example, the heart is shown only at end-expiration.

The heart image generation unit can be adapted to image the representation of the heart, if the bronchial tree is in one or several predetermined moving phases or respiratory phases, respectively. This predetermined moving or respiratory phase, or these predetermined moving or respiratory phases can be predetermined by a user or automatically.

It is further preferred that the bronchial tree image data set also shows the heart, wherein the heart image generation unit further comprises a registration unit for registering the representation of the heart and the bronchial tree image data set with respect to each other. In an embodiment, the registration unit is adapted to register the representation of the heart and the bronchial tree image data set with respect to each other by using the determined bronchial tree. In a further embodiment, the registration unit is adapted to use other markers or structures for registration, for example, the spine or fiducial markers. In an embodiment, the registration unit can be adapted to register the representation of the heart and the bronchial tree image data set with respect to each other in advance, with or without considering the bronchial tree, and then this registration can be corrected by using the movement of the bronchial tree, which has been determined from the bronchial tree image data set.

The bronchial tree image data set comprises preferentially two-dimensional projection images measured at different points in time and the representation of the heart is preferentially a three-dimensional model of the heart, wherein for at least one point in time a 2D-3D registration is performed for registering at least one of the two-dimensional projection images with the three-dimensional heart model. In another embodiment, the registration unit is adapted to perform a 2D-3D registration of a two-dimensional projection image with a three-dimensional heart image data set, for example, by using bones shown in the projection image and in the heart image data set, wherein the representation of the heart is determined from the heart image data set and, thus, by registering the heart image data set the representation of the heart is registered. A 2D-3D registration method is, for example, disclosed in G. P. Penney, J. Weese, J. A. Little, P. Desmedt, D. L. G. Hill, and D. J. Hawkes, "A comparison of similarity measures for use in 2-D-3-D medical image registration," *IEEE Trans. Med. Imag.*, vol. 17, no. 4, pp. 586-595, April 1998.

If in an embodiment, the heart image data set and, thus, the representation of the heart, which is preferentially a heart model, and the bronchial tree image data set are obtained by 3D rotational angiography performed in the same X-ray imaging system, then the representation of the heart and the bronchial tree image data set, which comprises, in this embodiment, two-dimensional X-ray projection images, are directly registered with respect to each other, because the reference coordinate system is the same for the representation of the heart and for the bronchial tree image data set, and the registration unit can be omitted.

It is further preferred that the heart image generation unit comprises a heart movement determination unit for determining a movement of the heart from the determined information about respiration and a heart moving unit for moving the representation of the heart with respect to the registered bronchial tree image data set in accordance with the determined movement of the heart, wherein the heart image generation unit is adapted to generate an image showing the moving representation of the heart. This allows generating an image of the heart, wherein the representation of the heart moves with respect to the bronchial tree image data set, in particular, with respect to the preferred two-dimensional projection images. In particular, it is possible that the registration is separated from a movement correction with respect to respiration. For example, the registration can be performed firstly by using a known registration method like spine registration, and then, for example, during an interventional procedure, the representation of the heart can be moved with respect to the bronchial tree image data set and in accordance with the determined information about respiration, i.e. e.g. in accordance with the determined movement of the bronchial tree or determined respiratory phases, in order to show the movement of the heart caused by respiration.

It is further preferred that the heart image generation unit further comprises an overlay image data set generation unit for generating an overlay image data set by overlaying the representation of the heart and the bronchial tree image data set, which have been registered with respect to each other. This allows showing the bronchial tree image data set, which is preferentially a temporal sequence of two-dimensional fluoroscopy projection images, overlaid with the representation of the heart, which preferentially moves in accordance with respiration.

In an embodiment, the respiration determination apparatus comprises a representation providing unit for providing a representation of a heart of the person being a first input for receiving a three-dimensional model of at least a part of the heart, the bronchial tree image data set providing unit is a second input for receiving the bronchial tree image data set being two-dimensional images of a region comprising the at least part of the heart, the respiration determination apparatus comprises a heart image generation unit for generating an image showing the representation of the heart, wherein the heart image generation unit further comprises a registration unit for registering the representation of the heart and the bronchial tree image data set with respect to each other, wherein the registration unit is a means for registering the two-dimensional images with the three-dimensional model, the bronchial tree detection unit is a means for estimating motion of the tracheal bifurcation from the two-dimensional images, the heart image generation unit is a means for correcting the registration of the two-dimensional images on the basis of the estimated motion.

In a further aspect of the present invention a respiration determination method for determining respiration of a person is presented, the method comprising following steps:
- providing a bronchial tree image data set showing a bronchial tree,
- detecting the bronchial tree in the bronchial tree image data set,
- determining information about the respiration from the detected bronchial tree.

In a further aspect of the present invention a respiration determination computer program for determining respiration of a person is presented, wherein the computer program comprises program code means for causing the respiration determination apparatus to carry out the steps of the respiration determination method, when the computer program is run on a computer controlling the respiration determination apparatus.

It shall be understood that a preferred embodiment of the invention can be any combination of the dependent claims with the respective independent claim.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
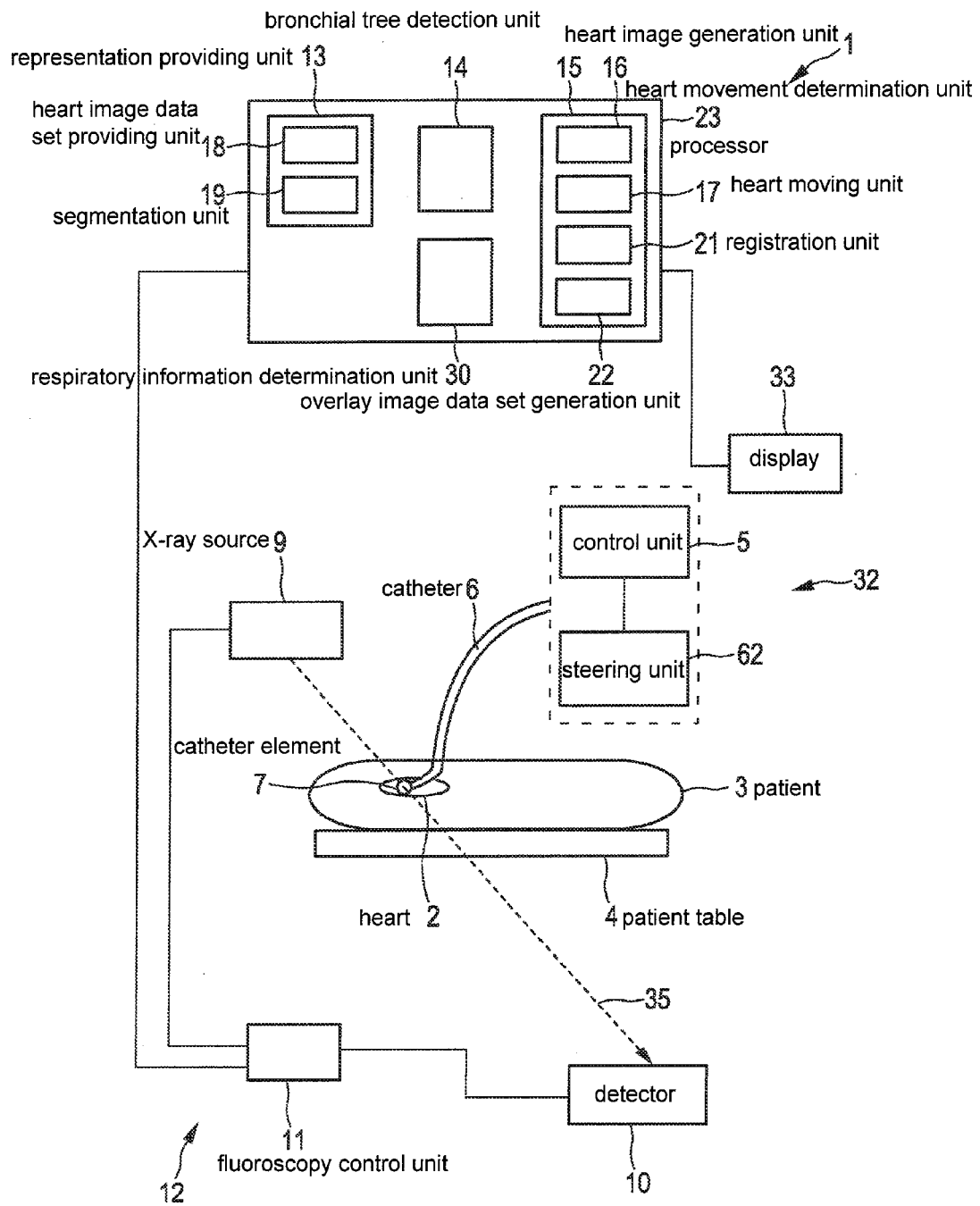
FIG. 1 shows schematically and exemplary an embodiment of a respiration determination apparatus for determining respiration of a person and a catheter device.

FIG. 1 shows schematically and exemplarily an embodiment of a respiration determination apparatus for determining respiration. The apparatus 1 comprises a representation providing unit 13 for providing a representation of a heart 2 of a patient 3. In FIG. 1, the patient 3 with the heart 2 is shown schematically located on a patient table 4. A projection 24 of the representation of the heart 2 registered on a bronchial tree image data set is schematically and exemplarily shown in FIG. 2. In the embodiment shown in FIG. 2, the projection 24 of the registered representation represents the anatomy of the left atrium of the heart.

In this embodiment, the representation providing unit 13 comprises a heart image data set providing unit 18 for providing a heart image data set showing the heart, wherein the representation providing unit 13 is adapted to provide the representation of the heart based on the heart image data set. The representation providing unit 13 further comprises a segmentation unit 19 for segmenting the heart in the heart image data set for providing the representation of the heart. Known segmentation methods, which can be used for segmenting the heart in the heart image data set, are, for example, a region growing method or the use of a general adaptive heart shape model, which is adapted to the current heart image data set. This allows providing a representation of the heart, which is preferentially a two- or three-dimensional heart model, which fits to the heart being currently imaged.

In another embodiment, a model of the heart is provided without performing a segmentation step, i.e. the segmentation step is optional. The model of the heart can simply be a function that gives the three-dimensional deformation of the model at each phase. This function can represent a "mean" model of the heart and its deformations. It can be obtained by studying the heart of several patients (from a CT for e.g.) and finding the model that best suits each heart position (at each phase) for all patients. If the deformation is needed it can easily be extrapolated from two consecutive positions of the mean model.

The heart image data set providing unit is preferentially a computed tomography imaging device, a magnetic-resonance imaging device, a nuclear imaging device like a positron emission tomography device or a single photon emission tomography device or another imaging device for generating an image data set of the heart. The heart image data set providing unit can also be a storing unit, in which the heart image data set is stored already. Also the representation providing unit can be a storing unit, in which the representation of the heart is stored already, but preferentially the representation of the heart shows a heart of current person, which is determined by using the heart image data set provided by the heart image data set providing unit.

In an embodiment, the heart image data image data set providing unit is adapted to provide a multi-phase heart image data set, which shows the heart in different respiration phases, wherein the representation providing unit is adapted to provide different representations of the heart, which correspond to different respiratory phases, based on the multi-phase heart image data set, in particular, by segmenting the heart in the different respiratory phases. In an embodiment, in order to assign to the segmented hearts the respective phase, a reference image data set is used, which shows a heart in different known phases, and the image reference image data set is registered with the multi-phase image data set showing the heart or the segmentation of the heart of the current person.

The representation of the heart is preferentially a two- or three-dimensional model. If the representation consists of segmentations of the heart, which have been segmented for different respiratory phases, this representation can be defined by the function $M_i(\phi)$, which gives the three-dimensional position of an anatomical point of the heart. For example, the heart can be modeled by a set of surface points denoted by $M_i(\phi)$, wherein the index i indicates different locations on the surface of the representation, i.e. of the heart model, and $\phi$ denotes the respiratory phase. In another preferred embodiment, the representation of the heart can also depend on other variables like the cardiac phase.

It should be noted that also the projection 24 itself could be regarded as representation of the heart.

The respiration determination apparatus 1 further comprises a bronchial tree image data set providing unit 12 for providing a temporal dependent bronchial tree image data set showing a tracheal bifurcation 26. The tracheal bifurcation 26 and a two-dimensional projection image 25 of the temporal dependent bronchial tree image data set are schematically and exemplarily shown in FIG. 2. The bronchial tree image data set providing unit 12 is, in this embodiment, a fluoroscopy image data set providing unit, i.e. a fluoroscopy device, for providing a fluoroscopy image data set being the bronchial tree image data set. The fluoroscopy image data set is preferentially a set of two-dimensional projection images, which are acquired at different points in time.

The fluoroscopy device 12 comprises an X-ray source 9 and a detection unit 10, which are controlled by a fluoroscopy control unit 11. The fluoroscopy device 12 generates X-ray projection images of the heart 2 and preferentially of a catheter element 7 of a catheter 6, which will be described further below. The X-rays of the X-ray source 9 are schematically indicated by the arrow 35.

The respiration determination apparatus further comprises a bronchial tree detection unit 14 for detecting the bronchial tree in the bronchial tree image data set and a respiratory information determination unit 30 for determining information about the respiration from the detected bronchial tree 26.

Preferentially, the bronchial tree image data set comprises several bronchial tree images 25 showing the bronchial tree 26 at different points in time and the bronchial tree detection unit 14 is adapted to detect a movement of the bronchial tree in the bronchial tree image data set, wherein the respiratory information determination unit 30 is adapted to determine the movement of the bronchial tree as the information about the respiration. It is further preferred that the bronchial tree detection unit 14 is adapted to segment the bronchial tree in the several bronchial tree images showing the bronchial tree at different points in time for generating segmented bronchial trees that correspond to different points in time, which form the bronchial tree movement. The determined movement is preferentially described as a translation and/or a rotation of the bronchial tree, in particular, of the segmented bronchial tree. If the bronchial tree image data set is a set of two-dimensional projection images, which have been acquired at different points in time, the determined movement of the bronchial tree is preferentially described as a translation and/or a rotation in the projection plane of the two-dimensional projection images. Since the bronchial tree moves with respiration and, thus, the movement of the bronchial tree is caused by respiration, the movement of the bronchial tree is information about the respiration, which can be obtained with good quality from the bronchial tree image data set.

In an embodiment, the segmentation of the bronchial tree is performed by extracting contours in the bronchial tree image data set and by grouping these contours together such that the grouped contours are consistent with a priori information about the anatomy of the bronchial tree, for example, such that they are consistent with a priori information about the bronchial tree outline. In other embodiment, the segmentation of the bronchial tree can be performed by using other, known segmentation methods.

The respiration determination apparatus 1 further comprises a heart image generation unit 15 for generating an image 27 showing the representation of the heart 2 depending on the determined information about the respiration. In this embodiment, the heart image generation unit 15 comprises a heart movement determination unit 16 for determining a movement of the heart from the determined information about the respiration and a heart moving unit 17 for moving the representation of the heart in accordance with the determined movement of the heart, wherein the heart image generation unit 15 is adapted to generate an image showing the moving representation of the heart.

Furthermore, the bronchial tree image data set comprises several bronchial tree images showing the bronchial tree at different points in time and the bronchial tree detection unit 14 is adapted to detect a movement of the bronchial tree in the bronchial tree image data set. The respiratory information determination unit 30 is adapted to determine the movement of the bronchial tree as the information about the respiration and the heart movement determination unit 16 is adapted to determine the movement of the heart as the determined movement of the bronchial tree. If it is assumed that the heart, in particular, the left atrium, moves rigidly with the bronchial tree, in particular, the tracheal bifurcation, the movement of the heart and the movement of the bronchial tree are the same and the heart movement determination unit is adapted to determine the movement of the heart, in particular, the movement of the left atrium, as the movement of the bronchial tree, in particular, of the tracheal bifurcation. The heart moving unit is then adapted to move the heart by adding the determined movement of the bronchial tree to the representation of the heart, which is shown by the heart image generation unit. Preferentially, if the bronchial tree 26, i.e. preferentially the tracheal bifurcation, shown in the two-dimensional projection image 25 rotates, in particular around the projection line, and/or translates in the projection plane, also the projection 24 of the representation of the heart is rotated and/or translated, wherein the bronchial tree 26 and the projection 24 of the representation of the heart move, in particular, rotate and/or translate, similarly.

The determined movement of the bronchial tree is periodical and comprises several moving phases, wherein the heart image generation unit 15 is adapted to image the representation of the heart, if the bronchial tree is in a predetermined moving phase. The moving phases of the movement of the bronchial tree correspond to the respiration phases, and the representation of the heart is therefore preferentially only shown, for example, overlaid over the bronchial tree image data set, which is preferentially a temporal sequence of two-dimensional fluoroscopy projection images, if a certain respiration phase is present. For example, the representation of the heart is only shown at end-expiration.

In this embodiment, the bronchial tree image data set also shows the heart 2 and the heart image generation unit 15 further comprises a registration unit 21 for registering the representation of the heart 2 and the bronchial tree image data set 25, i.e. the two-dimensional fluoroscopy projection image, with respect to each other. The heart image generation unit 15 further comprises an overlay image data set generation unit 22 for generating an overlay image data set 27 by overlaying the representation of the heart 2 and the bronchial tree image data set 25, which have been registered with respect to each other.

The registration unit 21 can be adapted to register the representation of the heart and the bronchial tree image data set with respect to each other by using the determined bronchial tree, in particular, by using the tracheal bifurcation. Alternatively or in addition, the registration unit can be adapted to use other markers or structures for registration, for example, the spine or fiducial markers. In an embodiment, the registration unit can be adapted to register the representation of the heart and the bronchial tree image data set with respect to each other in advance, with or without considering the bronchial tree, and then this registration can be corrected by using the determined movement of the heart. In particular, the heart moving unit 17 can be adapted to move the representation of the heart in accordance with the determined movement of the heart with respect to the registered bronchial tree image data set, i.e., in a preferred embodiment, the representation of the heart 2 and the bronchial tree image data set 25 are initially registered with respect to each other, for example, for a given respiration phase, the representation 24 of the heart 2 is overlaid on the bronchial tree image data set, which have been registered with respect to each other, and the representation 24 of the heart 2 is moved with respect to the bronchial tree image data set, which is, in this embodiment, a two-dimensional fluoroscopy projection image, in accordance with the determined movement of the heart 2, which is a movement caused by respiration. Thus, dynamically and in real time the representation of the heart 2 can be shown overlaid on the two-dimensional fluoroscopy projection image 25, while this representation is moving in accordance with respiration.

The bronchial tree image data set comprises preferentially two-dimensional projection images measured at different points in time and the representation of the heart is preferentially a three-dimensional model of the heart, wherein for at least one point in time a 2D-3D registration is performed for registering at least one of the two-dimensional projection images with the three-dimensional heart model. In another embodiment, the registration unit is adapted to perform a 2D-3D registration of a two-dimensional projection image with a three-dimensional heart image data set, for example, by using bones shown in the projection image and in the heart image data set, wherein the representation of the heart is determined from the heart image data set and, thus, by registering the heart image data set the representation of the heart is registered. A 2D-3D registration method is, for example, disclosed in G. P. Penney, J. Weese, J. A. Little, P. Desmedt, D. L. G. Hill, and D. J. Hawkes, "A comparison of similarity measures for use in 2-D-3-D medical image registration," *IEEE Trans. Med. Imag.*, vol. 17, no. 4, pp. 586-595, April 1998.

If in another embodiment, the heart image data set and, thus, the representation of the heart, which is preferentially a heart model, and the bronchial tree image data set are obtained by 3D rotational angiography performed in the same X-ray imaging system, then the representation of the heart and the bronchial tree image data set, which comprises, in this embodiment, two-dimensional X-ray projection images, are directly registered with respect to each other, because the reference coordinate system is the same for the representation of the heart and for the bronchial tree image data set, and the registration unit can be omitted.

The respiration determination apparatus further comprises a display 33, on which the overlay image data set is preferentially displayed. In another embodiment, alternatively or in addition, the display can be adapted to show the representation of the heart and/or the heart image data set and/or the bronchial tree image data set.

FIG. 1 shows further schematically and exemplarily a catheter device 32 for applying energy to tissue and sensing this tissue inside the heart 2. The catheter device 32 comprises one or several catheters, wherein one catheter is shown in FIG. 1. The catheter 6 comprises a catheter element 7, which could be an energy application element or a sensing element for applying energy to tissue inside the heart or for sensing the tissue, respectively. The catheter element 7 is schematically indicated in FIG. 1 by a circle 7. This circle 7 should not be construed as limiting the catheter element to a certain shape. For example, the catheter element 7 could also be rectangular.

The catheter element 7 is connected to a control unit 5 via the catheter 6. The catheter 6 with the catheter element 7, which comprises, for example, electrodes and/or optical fibers, can be introduced into the heart 2, wherein the catheter 6 is steered and navigated to the heart chambers by a steering unit 62 using build-in guiding means (not shown). In another embodiment, the steering unit 62 can comprise an introducer for steering and navigating the catheter 6 to guide the catheter passively into the heart 2. The steering unit 62 can be adapted for steering the catheter element 7 manually and/or the steering unit 62 can comprise a robotic system for robotically steering the catheter element 7. This allows steering the catheter element 7 to a desired region within the heart 2, in particular, at an endocardial surface of a heart chamber. The dashed box in FIG. 1 indicates that both, the control unit 5 and the steering unit 62, are coupled to the catheter 6 comprising the catheter element 7.

During introducing the catheter element 7 and the catheter 6 into the heart 2, the fluoroscopy device 12 generates a temporal dependent bronchial tree image data set showing the tracheal bifurcation, the heart 2 and the catheter element 7, wherein, in this embodiment, the temporal dependent bronchial tree image data set is a set of two-dimensional fluoroscopy projection images, which are acquired at different points in time. This fluoroscopy device 12 preferentially generates two-dimensional fluoroscopy projection images of the heart 2, the tracheal bifurcation and the catheter element 7, also if the catheter element 7 is already located within the heart 2.

Figure 2:
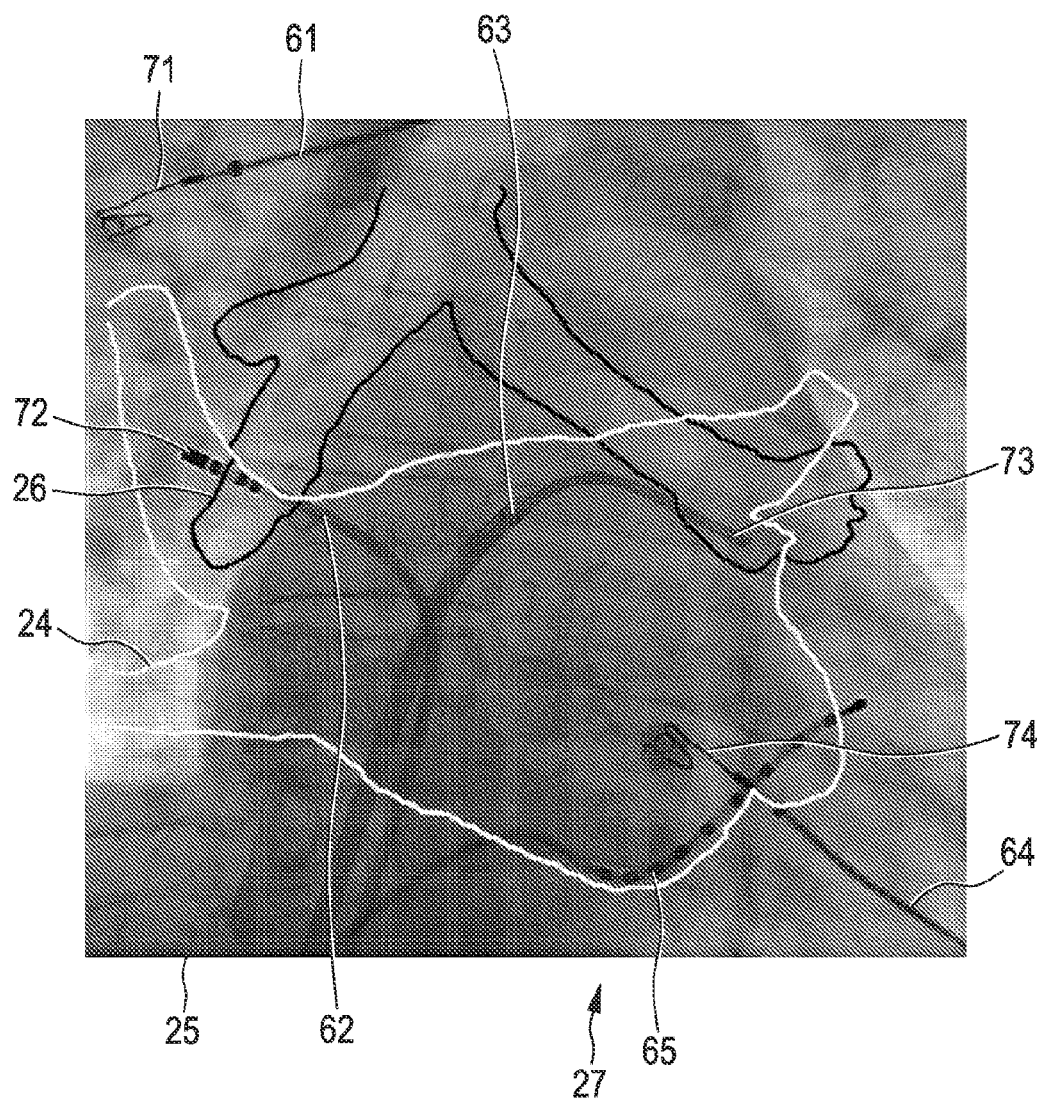
FIG. 2 shows a bronchial tree image overlaid with a representation of a heart.

FIG. 2 shows schematically and exemplarily a two-dimensional fluoroscopy projection image 25 of a bronchial tree image data set with the overlaid and registered projection 24 of the representation of the heart 2. This two-dimensional fluoroscopy projection image shows the tracheal bifurcation 26 and some catheters 61 . . . 64 with catheter elements 71 . . . 74. This overlay image is preferentially shown on the display 33 such that the projection 24 of the representation of the heart moves in accordance with the movement of the tracheal bifurcation 26 and, thus, in accordance with respiration. In FIG. 2 the catheter elements 71 and 74 are electrocardiogram stitches, the catheter element 72 is an ablation catheter and the catheter element 73 is an injection catheter. FIG. 2 further shows a reference catheter 65.

In this embodiment, the representation providing unit 13, the bronchial tree detection unit 14, the heart image generation unit 15 and the respiratory information determination unit 30 are included in a processing unit 23.

Figure 3:
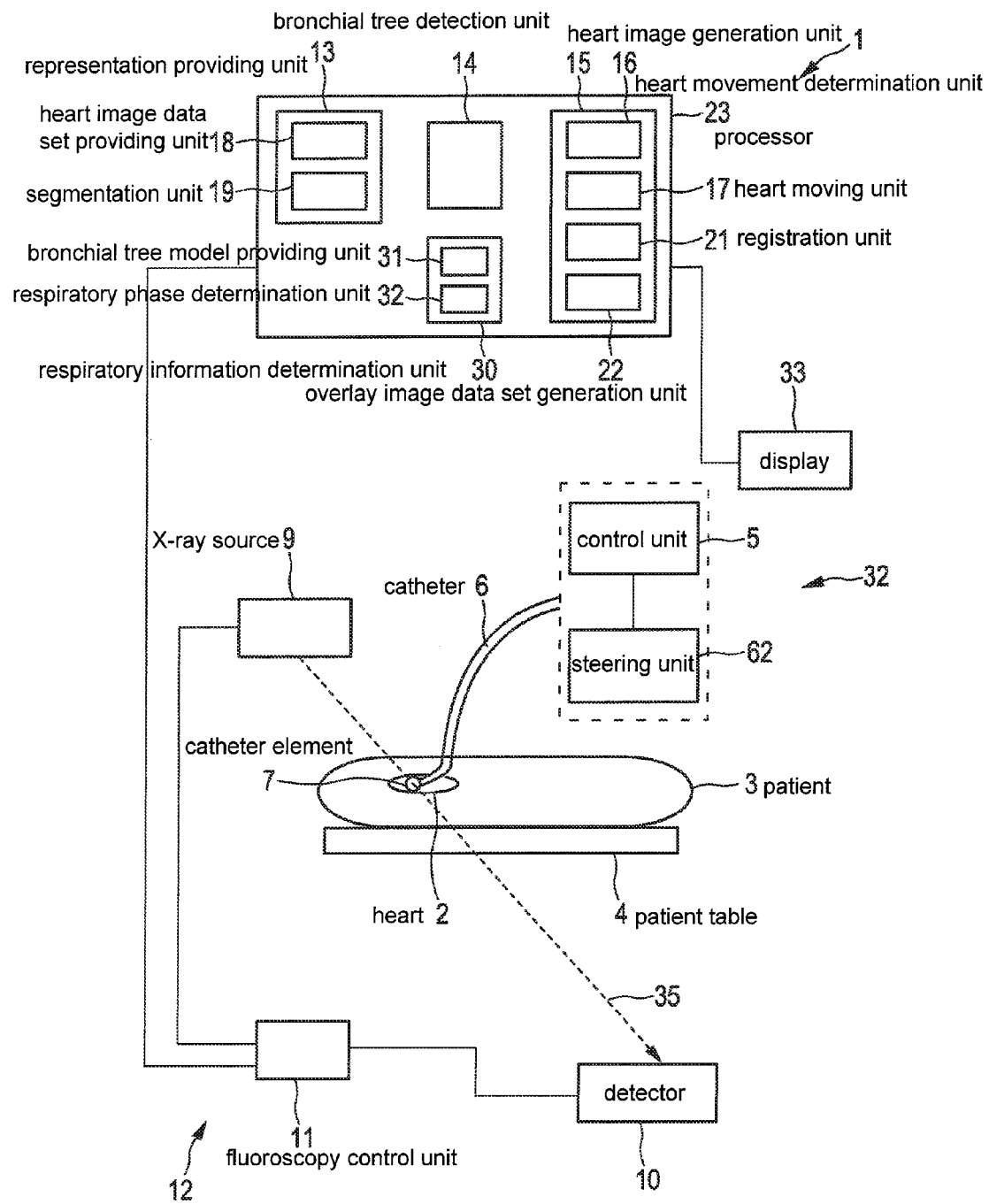
FIG. 3 shows schematically and exemplary another embodiment of a respiration determination apparatus for determining respiration of a person and a catheter device.

In another embodiment, which is schematically and exemplarily shown in FIG. 3, in which elements, which are similar with respect to FIG. 1, are indicated by similar reference numbers, the respiration information determination unit 30 comprises a bronchial tree model providing unit 31 for providing a bronchial tree model, which depends on a respiratory phase, and a respiratory phase determination unit 32 for determining a respiratory phase of the person by determining the respiratory phase, at which the bronchial tree model is most similar to the detected bronchial tree, wherein the determined respiratory phase is the information about respiration. In this embodiment, the bronchial tree model is formed as a set of different bronchial tree models for different respiratory phases, wherein the respiratory phase determination unit is adapted to determine a respiratory phase of the person by determining the bronchial tree model, which is most similar to the detected bronchial tree, wherein the respiratory phase of the most similar bronchial tree model is determined as the information about respiration.

In an embodiment, the heart image data set providing unit is adapted to provide a multi-phase heart image data set, which also shows the bronchial tree in different respiratory phases, or the bronchial tree image data set providing unit 12 is adapted to provide a bronchial tree image data set showing the bronchial tree in different respiratory phases, wherein the bronchial tree providing unit 31 is adapted to provide different representations of the bronchial tree, which correspond to different respiratory phases, based on the multi-phase heart image data set or the bronchial tree image data set, in particular, by segmenting the bronchial tree for the different respiratory phases. In an embodiment, in order to assign to the segmented bronchial trees the respective respiratory phase, a reference image data set is used, which shows a bronchial tree in different known respiratory phases and the image reference image data set is registered with the multi-phase image data set showing the bronchial tree or the segmentation of the bronchial tree of the current person.

The bronchial tree model is preferentially a two- or three-dimensional model. The bronchial tree models for different respiratory phases can be defined by the function $P_j(\phi)$, which gives the two- or three-dimensional position of an anatomical point of the bronchial tree. For example, the bronchial tree can be modeled by a set of surface points of a three-dimensional model or contour points of a two-dimensional model denoted by $P_j(\phi)$, wherein the index j indicates different locations on the surface of a three-dimensional bronchial tree model or on a contour of a two-dimensional bronchial tree model with the respiratory phase $\phi$.

In this embodiment, the representation providing unit 13 is adapted to provide different representations of the heart, which correspond to different respiratory phases, i.e. in particular to provide $M_i(\phi)$. Furthermore, the bronchial tree image data set comprises several bronchial tree images showing the bronchial tree at different points in time and the bronchial tree detection unit 14 is adapted to detect the bronchial tree in the several bronchial tree images. The respiratory phase determination unit 30 is adapted to determine the respiratory phase for the several bronchial tree images for determining several respiration phases that correspond to the different points in time, and the heart movement determination unit 16 is adapted to determine a movement of the heart as a series of the representations of the heart, which correspond to the determined several respiratory phases, sorted in accordance with their respective points in time. Thus, preferentially the bronchial tree model $P_j(\phi)$ is used for determining the respiratory phases $\phi$ by comparing the detected bronchial trees, which correspond to different points in time, and the movement of the heart is determined as series of heart models $M_i(\phi)$, which correspond to the determined respiratory phases $\phi$.

In this embodiment, which is described with reference to FIG. 3, the heart image generation unit 15 is preferentially adapted to image the representation of the heart, if the determined respiratory phase is similar to a predetermined respiratory phase. Also this allows showing the heart only, if the certain respiratory phase has been determined, for example, the heart is shown only at end-expiration.

The heart image generation unit can be adapted to image the representation of the heart, if the bronchial tree is in one or several predetermined moving phases or respiratory phases, respectively. This predetermined moving or respiratory phase, or these predetermined moving or respiratory phases can be predetermined by a user or automatically.

Figure 4:
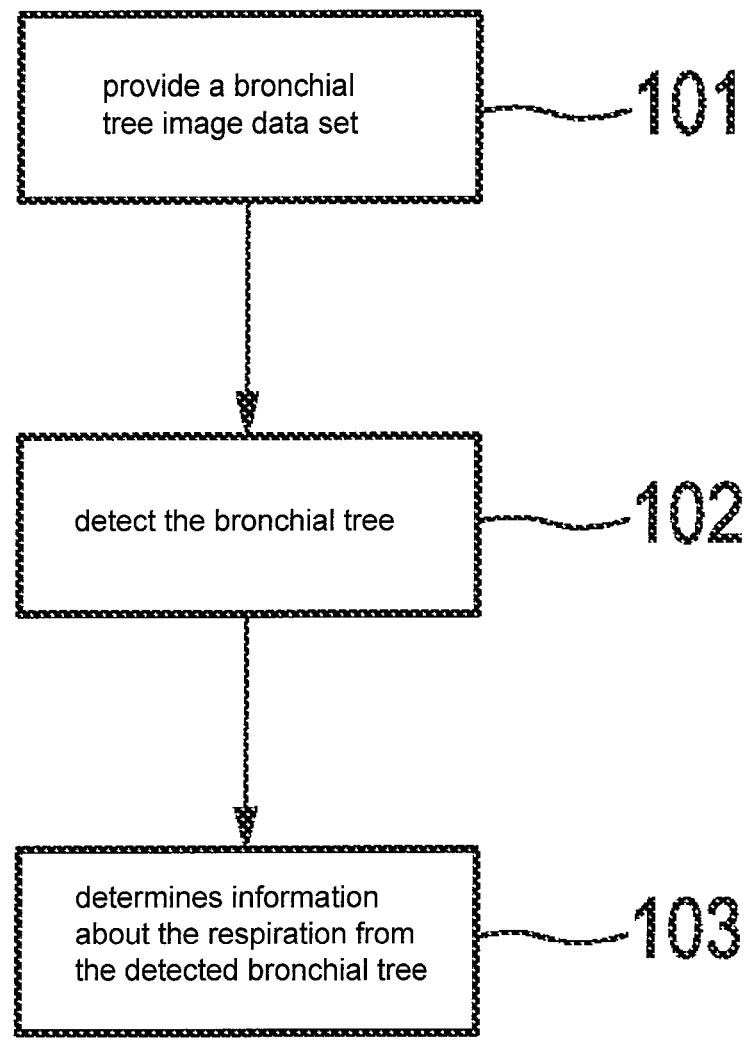
FIG. 4 shows a flow chart illustrating an exemplarily embodiment of a respiration determination method for determining respiration of a person.

In the following, an embodiment of a respiration determination method for determining respiration of a person will be described with reference to a flow chart shown in FIG. 4.

In step 101, the bronchial tree image data set providing unit 12 provides a bronchial tree image data set 25 showing a bronchial tree 26, and in step 102, the bronchial tree detection unit 14 detects the bronchial tree 26 in the bronchial tree image data set 25. In step 103, the respiratory information determination unit 30 determines information about the respiration from the detected bronchial tree 26. This information about respiration is preferentially a movement of the bronchial tree, because the bronchial tree moves with respiration, or the respiratory phase.

Steps 101 to 103 are preferentially performed at several points in time, in particular, continuously, allowing determining the movement of the bronchial tree or the respiratory phase at these several points in time. This determined movement or respiratory phase can be used for imaging the heart depending on respiration, for example, for showing the heart at certain moving or respiratory phases or for correcting a registration of the heart with respect to a fluoroscopy image.

The respiration determination apparatus and the catheter device are preferentially used in electrophysiology (EP) applications. EP is a specific domain of interventional cardiology where physicians use inter-cardiac catheters to locate and cure electrical dysfunctions of the heart rhythms under X-ray fluoroscopy guidance. A very challenging EP procedure is radio-frequency ablation for the treatment of the artrial fibrillation, which is also called AF. Another important procedure is a placement of a pacemaker for a cardiac resynchronization therapy (CRT) during which a pacemaker lead has to be placed in a coronary vein. In general, electrophysiologists need a special training to perfectly know the anatomy and the access pathways to all the sides of interest and some practice to select the correct devices and manipulate them to target.

EP procedures guided by fluoroscopy, and particularly AF, can take up to several hours. The main task of such procedures is to place the catheters at a given location inside the heart. The superimposition, i.e. the overlaying, of the target anatomical structures represented by the representation of the heart on fluoroscopy images, where they are not visible without contrast, is of a great help for the electrophysiologists.

In an embodiment, a three-dimensional model of the heart or of a part of the heart of the patient is generated before the intervention. In addition to this model, the three-dimensional position of the bronchial tree, in particular, of the tracheal bifurcation, is also known and its movement is correlated with the heart during respiration.

In a further step, the bronchial tree is detected and tracked in the sequence of fluoroscopy X-ray projection images during the intervention. This allows projecting the heart model over fluoroscopy, while enforcing relative positioning of the trachea. Tracking of the bronchial tree therefore allows movement compensated registration of the heart during the intervention, which is an advantage over other kinds of registration, for example, over spine-based registrations, where respiratory movements cannot be compensated for.

Although in the above described embodiments the heart image data set providing unit is preferentially a storing unit, in which a heart image data set is provided, which has been generated by a computed tomography respiration determination apparatus or a magnetic-resonance apparatus, this heart image data set can also be generated by another imaging device like a three-dimensional rotational angiography device or any other modality capable of acquiring a three-dimensional volume of the heart anatomy.

The representation providing unit can be adapted to segment the heart or a part of the heart, for example, the atrium, the coronary veins et cetera, wherein the segmented heart or the segmented part of the heart is the representation of the heart being a three-dimensional model of the heart. In an embodiment, the position of the bronchial tree with respect to the heart model is known. For example, the trachea can be segmented in the same provided heart image data set, which gives the relative positioning of the two organs.

The fluoroscopy device is preferentially configured to produce two-dimensional fluoroscopy images of the same anatomical region. The fluoroscopy device does not allow clear visualization of complex soft tissue anatomy such as the heart. By contrast, the bronchial tree provides a visual landmark in fluoroscopy which can be detected and tracked over time. The bronchial tree can be registered with the three-dimensional model of the heart. This gives the transformation to apply to overlay the heart model on top of the two-dimensional fluoroscopy image at a given respiratory phase.

The bronchial tree detection unit 14 is preferentially adapted to determine in-plane movements, i.e. translations in the plane of the two-dimensional fluoroscopy projection unit and rotations around the projection axis. This allows following respiratory movements in an antero-posterior view.

If the heart image data set providing unit provides an image data set of a three-dimensional rotational angiography device, which has been used to reconstruct an image of the left atrium in the same X-ray system and which is also the bronchial tree image data set providing unit being a fluoroscopy device like, for example, the so called ATG of Philips, a three-dimensional heart image data set is reconstructed in the same coordinate system as the two-dimensional fluoroscopy projection data set. In this case, a registration of the representation of the heart, which is obtained from the heart image data set, with the two-dimensional fluoroscopy projection image is not needed, because the heart image data set, which is preferentially three-dimensional, and, thus, the representation of the heart and the two-dimensional fluoroscopy projection image are aligned already. The tracking of the trachea, i.e. the determination of the movement of the bronchial tree, can then be used to compensate for respiration. Furthermore, in another embodiment, the registration unit can be adapted to register the representation of the heart with the bronchial tree image data set, i.e. preferentially with a two-dimensional fluoroscopy projection image of the temporal dependent bronchial tree image data set, by using spine-based registration or by using any other anatomical landmark, for example, the bronchial tree, to align the representation of the heart with the bronchial tree image data set. Then, the tracking of the bronchial tree, i.e. the determination of the movement of the bronchial tree, can be used to compensate for respiration.

The provided representation of the heart can also depend on the cardiac phase, wherein, if the heart is shown on the display 33, the cardiac phase is provided by a cardiac phase providing unit like an electrocardiograph and the representation of the heart is moved on the display depending on the provided cardiac phase and depending on the movement of the heart caused by respiration, which has been determined as described above.

Although in the above described embodiments a registration procedure is illustrated, the invention is not limited to the use of registration. The respiration determination apparatus, method and computer program define a determination of information about respiration, i.e. the movement of the bronchial tree or the respiratory phase, without the need of performing a registration procedure.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

The calculations and determinations, for example, the determinations of movements and respiratory phases, the segmentations and the registrations, performed by one or several units or devices can be performed by any other number of units or devices. The calculations and determinations and/or the control of the respiration determination apparatus in accordance with respiration determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A respiration determination apparatus for determining respiration of a person, the apparatus comprising: a bronchial tree image data set provider configured to provide a bronchial tree image data set showing a bronchial tree; a bronchial tree detector configured to detect the bronchial tree in the bronchial tree image set; a respiratory information determiner configured to determine information about the respiration from the detected bronchial tree representation provider configured to provide a representation of a heart of the person; and a heart image generator configured to generate an image showing the representation of the heart depending on the determined information about the respiration, wherein the bronchial tree image data set comprises several bronchial tree images, showing the bronchial tree at different points in time, wherein the bronchial tree detector is further configured to detect a movement of the bronchial tree in the bronchial tree image data set, and wherein the respiratory information determiner is further configured to determine the movement of the bronchial tree as the information about the respiration for generating the image showing the representation of the heart depending on the determined movement of the bronchial tree.

2. The respiration determination apparatus as claimed in claim 1, wherein the bronchial tree detector is further configured to segment the bronchial tree in the several bronchial tree images showing the bronchial tree at different points in time for generating segmented bronchial trees that correspond to different points in time, which form the bronchial tree movement.

3. The respiration determination apparatus as claimed in claim 1, wherein the respiration information determiner comprises:
a bronchial tree model provider configured to provide a bronchial tree model, which depends on a respiratory phase;
a respiratory phase determiner configured to determine a respiratory phase of the person by determining the respiratory phase, at which the bronchial tree model is most similar to the detected bronchial tree, wherein the determined respiratory phase is the information about respiration.

4. The respiration determination apparatus as claimed in claim 1, wherein the bronchial tree image data set provider is a fluoroscopy image data set provider configured to provide a fluoroscopy image data set being the bronchial tree image data set.

5. The respiration determination apparatus as claimed in claim 1, wherein the heart image generator comprises: a heart movement determiner configured to determine a movement of the heart from the determined information about the respiration; and a heart mover configured to move the representation of the heart in accordance with the determined movement of the heart, wherein the heart image generator is adapted to generate an image showing the moving representation of the heart.

6. The respiration determination apparatus as claimed in claim 5, wherein the bronchial tree image data set comprises several bronchial tree images showing the bronchial tree at different points in time, the bronchial tree detector is further configured to detect a movement of the bronchial tree in the bronchial tree image data set, the respiratory information determiner is further configured to determine the movement of the bronchial tree as the information about the respiration, the heart movement determiner is further configured to determine the movement of the heart as the determined movement of the bronchial tree.

7. The respiration determination apparatus as claimed in claim 5, wherein the representation provider is further configured to provide to provide different representations of the heart, which correspond to different respiratory phases, the respiration information determiner further comprises:

a bronchial tree model provider configured to provide a bronchial tree model, which depends on a respiratory phase, a respiratory phase determiner configured to determine a respiratory phase of the person by determining the respiratory phase, at which the bronchial tree model is most similar to the detected bronchial tree, wherein the determined respiratory phase is the information about respiration, the bronchial tree image data set comprises several bronchial tree images showing the bronchial tree at different points in time, the bronchial tree detector is further configured to detect the bronchial tree in the several bronchial tree images, the respiratory phase determiner is further configured to determine the respiratory phase for the several bronchial tree images for determining several respiration phases that correspond to the different points in time, the heart movement determiner is further configured to determine a movement of the heart as a series of the representations of the heart, which correspond to the determined several respiratory phases, sorted in accordance with their respective points in time.

8. The respiration determination apparatus as claimed in claim 1, wherein the bronchial tree image data set comprises several bronchial tree images showing the bronchial tree at different points in time, the bronchial tree detector further configured to detect a movement of the bronchial tree in the bronchial tree image data set, and the respiratory information determiner is further configured to determine the movement of the bronchial tree as the information about the respiration, the determined movement of the bronchial tree is periodical and comprises several moving phases, wherein the heart image generator is further configured to image the representation of the heart if the bronchial tree is in a predetermined moving phase.

9. The respiration determination apparatus as claimed in claim 1, wherein the respiration information determiner comprises: a bronchial tree model provider configured to provide a bronchial tree model, which depends on a respiratory phase; a respiratory phase determiner configured to determine a respiratory phase of the person by determining the respiratory phase, at which the bronchial tree model is most similar to the detected bronchial tree, wherein the determined respiratory phase is the information about respiration; the heart image generator is further configured to image the representation of the heart, if the determined respiratory phase is similar to a predetermined respiratory phase.

10. The respiration determination apparatus as claimed in claim 1, wherein the respiration determination apparatus further comprises a representation provider configured to provide a representation of a heart of the person being a first input for receiving a three-dimensional model of at least a part of the heart, the bronchial tree image data set provider is a second input for receiving the bronchial tree image data set being two-dimensional images of a region comprising the at least part of the heart, the respiration determination apparatus comprises a heart image generator configured to generate an image showing the representation of the heart, wherein the heart image generator further comprises a registrator configured to register the representation of the heart and the bronchial tree image data set with respect to each other, wherein the registrator is further configured to register the two-dimensional images with the three-dimensional model, the bronchial tree detector comprises an estimator configured to estimate motion of the tracheal bifurcation from the two-dimensional images, the heart image generator comprises a corrector configured to correct registration of the two-dimensional images based on the estimated motion.

11. A respiration determination method for determining respiration of a person, the method comprising the act of:

providing a bronchial tree image data set showing a bronchial tree;

detecting the bronchial tree in the bronchial tree image data set, including detecting a movement of the bronchial tree in the bronchial tree image data set;

providing a representation of a heart of the person;

determining information about the respiration from the detected bronchial tree including determining the movement of the bronchial tree as the information about the respiration for generating the image showing the representation of the heart depending on the determined movement of the bronchial tree; and displaying on a display an image showing the representation of the heart depending on the determined information about the respiration, wherein the bronchial tree image data set comprises several bronchial tree images showing the bronchial tree at different points in time.

12. A non-transitory computer readable medium embodying respiration determination computer program for determining respiration of a person, wherein the computer program comprises instructions for causing a respiration determination apparatus to determine respiration of a person, the apparatus comprising:

a bronchial tree image data set providing unit for providing a bronchial tree image data set showing a bronchial tree;

a bronchial tree detection unit for detecting the bronchial tree in the bronchial tree image data set;

a respiratory information determination unit for determining information about the respiration from the detected bronchial tree; wherein the instructions, when executed by a processor, configure the processor to perform the acts of:

providing a bronchial tree image data set showing a bronchial tree;

detecting the bronchial tree in the bronchial tree image data set including detecting a movement of the bronchial tree in the bronchial tree image data set;

providing a representation of a heart of the person;

determining information about the respiration from the detected bronchial tree including determining the movement of the bronchial tree as the information about the respiration for generating the image showing the representation of the heart depending on the determined movement of the bronchial tree; and displaying on a display an image showing the representation of the heart depending on the determined information about the respiration,
wherein the bronchial tree image data set comprises several bronchial tree images showing the bronchial tree at different points in time.

* * * * *